(12) United States Patent
Huang

(10) Patent No.: US 6,660,871 B2
(45) Date of Patent: Dec. 9, 2003

(54) SYNTHESIS OF 4H-CHROMENE DERIVATIVES

(75) Inventor: Ziwei Huang, Champaign, IL (US)

(73) Assignee: Thomas Jefferson Unversity, Philadelphia, PA (US)

( * ) Notice: Subject to any disclaimer, the term of this patent is extended or adjusted under 35 U.S.C. 154(b) by 0 days.

(21) Appl. No.: 10/062,641

(22) Filed: Feb. 1, 2002

(65) Prior Publication Data

US 2002/0161245 A1 Oct. 31, 2002

Related U.S. Application Data

(60) Provisional application No. 60/265,766, filed on Feb. 1, 2001.

(51) Int. Cl.[7] ...................... C07D 311/74; C07D 311/76
(52) U.S. Cl. ........................ 549/404; 549/407; 549/398
(58) Field of Search ................................. 549/404, 398, 549/407

(56) References Cited

U.S. PATENT DOCUMENTS 4,024,160 A * 5/1977 Brown et al. ................ 549/401
5,659,051 A * 8/1997 Higashii et al. ............. 549/401

OTHER PUBLICATIONS

Adams, J., & Cory, S. "The Bcl–2 Protein Family: Arbiters of Cell Survival." *Science* 281: 1322–1326, 1998.
Chao, D., & Korsmeyer, S. "BCL–2 Family: Regulators of Cell Death." *Annu. Rev. Immunol.* 16: 395–419, 1998.
Thompson, C. "Apoptosis in the Pathogenesis and Treatment of Disease." *Science* 267: 1456–62, 1995.
Reed, J. "Machanisms of Apoptosis Avoidance in Cancer." *Curr Opin Oncol* 1: 68–75, 1999.
Cosulich, S., Worrall, V., Hedge, P., Green, S., & Clarke, P. "Regulation of Apoptosis by BH3 Domains in a Cell–free System." *Current Biology* 7:913–920, 1997/.
Holinger, E., Chittenden, T., & Lutz, R. "Bak BH# Peptides Antagonize Bcl–$x_L$ Function and Induce Apoptosis through Cytochrome c–iindependent Activation of Caspases." *J Biol Chem* 274 (19): 13298–13304, 1999.
Wang, J., Zhang, Z., Choksi, S., Shan, S., Zhixian, L., Croce, C., Alnemri, E., Korngold, R., & Huang, Z. "Cell Permeable Bcl–2 Binding Peptides: A chemical approach to apoptosis Induction in Tumor Cells." *Cancer Research* 60: 1498–1502, 2000.
Wang, J., Liu, D., Zhang, Z., Shan, S., Han, X., Srinivasula, S., Croce, C., Alnemri, E., & Huang, Z. "Structure–based Discovery of an Organic Compound that Binds Bcl–2 Protein and Induces Apoptosis of Tumor Cells." *Proc Natl Acad Sci USA* 97 (13): 7124–7129, 2000.
Fujimoto, A. "A New Selective Preparation of 4H–Chromenes by Reaction of alkyl cyanoacetate with 3,5–Dibromosalicylaldehyde in the Presence of Ammonium Acetate." *Synthesis* 871–872, 1977.
Roudier, J., & Foucaud, A. "A Convenient Systhesis of 4H–Chromosomes." *Synthesis* 159–160, 1984.
Niefang Yu et al., *Tetrahedron Letters* 41: 6993–6996 (2000).

* cited by examiner

Primary Examiner—Alan L. Rotman
Assistant Examiner—Raymond Covington
(74) Attorney, Agent, or Firm—Drinker Biddle & Reath LLP

(57) ABSTRACT

Substituted 4H-chromene derivatives are a new class of compounds that bind to Bcl-2 protein and induce apoptosis in tumor cells. The present invention is directed to an efficient synthetic method for the preparation of these compounds from salicylaldehyde derivatives and alkyl cyanoacetates under solid phase.

10 Claims, 2 Drawing Sheets

HA14-1

HA14-1

SYNTHESIS OF 4H-CHROMENE DERIVATIVES

CONTINUING APPLICATION DATA

This application claims priority under 35 U.S.C. §119 based upon U.S. Provisional Patent Application No. 60/265,766 filed on Feb. 1, 2001.

FIELD OF THE INVENTION

The present invention relates to the fields of organic chemistry and molecular biology and, more particularly, is directed to a method for synthesizing 4H-chromene derivatives.

BACKGROUND OF THE INVENTION

Bcl-2 and a family of related proteins regulate apoptosis or programmed cell death and are implicated in a number of human diseases such as cancer. Specifically, Bcl-2 can contribute to neoplastic cell expansion by preventing normal cell turnover caused by physiological cell death mechanisms. High levels of Bcl-2 gene expression are found in a wide variety of human cancers and can lead to tumor cell resistance to conventional chemotherapy and radiotherapy. Synthetic peptides that bind to a functional surface pocket of Bcl-2 have in vitro activity for inducing apoptosis in cell-free systems and in HeLa cells. Furthermore, Bcl-2 binding peptides containing a fatty acid as a cell permeable moiety can induce apoptosis in vitro and have in vivo activity in slowing human myeloid leukemia growth in severe combined immunodeficient mice. These studies suggest that peptides or other small molecules targeted to the Bcl-2 surface pocket could have important clinical applications.

The organic compound HA14-1 (FIG. 1), a 4H-chromene derivative, exhibits binding activity for the surface pocket of Bcl-2 protein ($IC_{50}$ =9 $\mu$M) and induces apoptosis of tumor cells. The discovery of this Bcl-2 binding compound provides a promising lead compound for the development of potential anti-cancer agents and prompted the chemical synthesis of a series of HA14-1 analogs in order to study its structure-activity relationship and increase its potency.

While there are currently two methods for the preparation of 4H-chromene derivatives, both methods have limitations. The first method involves the cyclization of salicylaldehyde derivatives with alkyl cyanoacetates in the presence of ammonium acetate at 5–10° C., which produces analogs of HA14-1.

The reaction temperature (5–10° C.) is crucial for obtaining the desired products. If the temperature is just slightly raised to 15° C., the reaction will fail to give the desired product. In another procedure, aluminum oxide ($Al_2O_3$) is used as the catalyst instead of ammonium acetate. However, this procedure is further limited by low yields.

The present invention provides a procedure for the preparation of 4H-chromene derivatives that overcomes the limitations of the current methodology. In one embodiment of the present invention, molecular sieve, more particularly, molecular sieve 3Å, is used as the catalyst. This novel catalyst as disclosed in the present invention, allows the reaction to take place under milder conditions, about 15–300° C., and gives higher yields of 4H-chromene derivatives, about 86%.

DEFINITIONS

In the present invention, "4H-chromene derivatives", "HA14-1 derivatives" and "HA14-1 analogs" are used interchangeably. They include molecules of the formula:

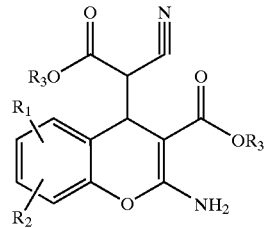

Within the scope of the present invention, but not being limited thereto, $R_1$ and $R_2$ are $CH_3$, $CH_2CH_3$, $CH_2CH=CH_2$, $CH_2Br$, $CF_3$, $NH_2$, OH, $OCH_3$, CN, $NO_2$, Cl, Br, F, COOH or $COOCH_3$; and, $R_3$ is selected from the group consisting of hydrogen, $CH_3$, $CH_2CH_3$, $CH_2CH_2CH_3$, $CH_2CH_2CH_2CH_3$, $C(CH_3)_3$, $CH_2Ph$ or $CH_2CH_2OCH_3$.

"structure-activity relationship" as used herein, means the relationship between the structure of a peptide or a molecule and its ability to bind to the functional surface pocket of Bcl-2, thus inhibiting the biological activity of Bcl-2 and inducing apoptosis in cancer cells.

DETAILED DESCRIPTION OF THE INVENTION

Figure 1:
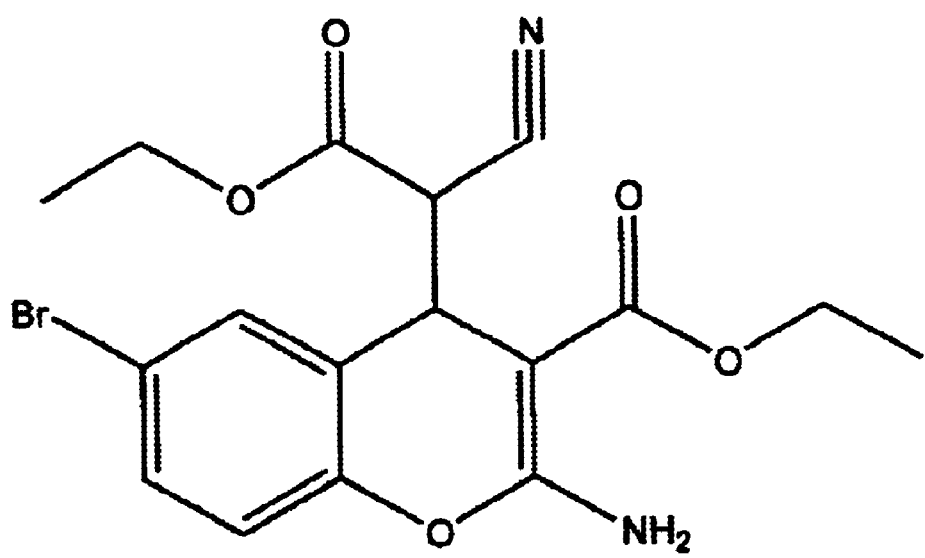
FIG. 1 illustrates the chemical structure of HA14-1.
Figure 2:
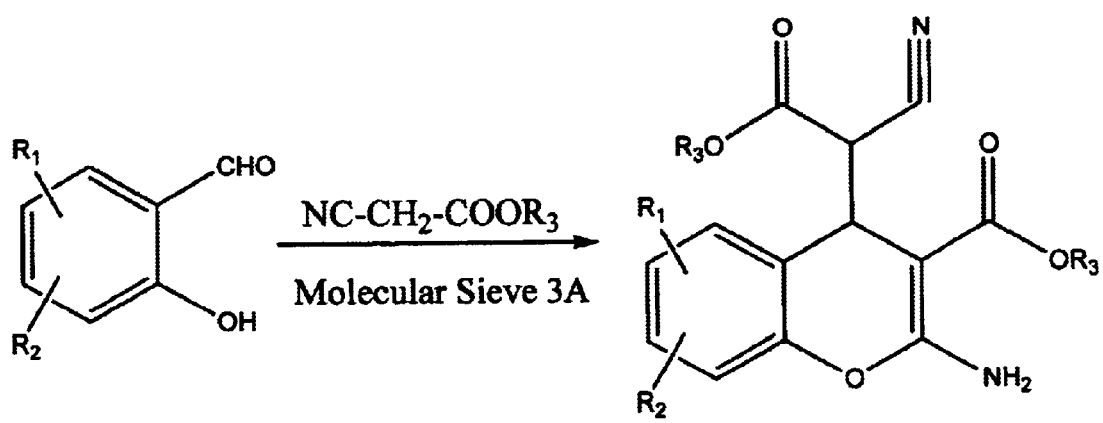
FIG. 2 illustrates the synthesis of 4H-chromene derivatives.

The present invention provides a method for preparing 4H-chromene derivatives. In the new method as disclosed herein, a salicylaldehyde derivative, an alkyl cyanoacetate, and a suitable molecular sieve were combined to produce a 4H-chromene derivative, as shown in FIG. 2. In one embodiment of the present invention molecular sieve 3Å was used as the catalyst to produce the 4H-chromene derivatives. In yet another embodiment of the present invention, the process is carried out at a temperature of about 15–30° C., for about 8–20 hours.

In still another embodiment of the present invention, the process is carried out at room temperature for 14 hours.

Synthesis of HA14-1

To a suspension of the 5-bromosalicylaldehyde (0.010 mol) in dry ethyl alcohol (30 ml) was added ethyl cyanoacetate (0.022 mol) and 3.0 grams of molecular sieve 3Å powder (Aldrich Chemical Company). The resulting mixture was stirred at room temperature overnight (14 h). Most of the 5-bromosalicylaldehyde disappeared within the first 2 hours as layer chromatography (TLC). The molecular sieve was then filtered off and washed 3 times with tetrahydrofuran. The filtrates were combined and the solvent was removed under vacuum. The residue solidified when incubated at −24° for 2 hours. The desired product was obtained by crystallization in 85% ethanol as a single diastereoisomeric pair. The yield was 86%.

Catalytic Activity of Other Catalysts

Other types of molecular sieves, such as molecular sieves 4Å and 5Å, as well as $Al_2O_3$, were also compared using this procedure. All solid catalysts tested catalyzed the reactions, with type-3Å giving the best yields. (Table 1).

TABLE 1

Comparison of various solid catalyst

| | Yield, % |
|---|---|
| Molecular sieve 3Å | 86.1 |
| Molecular sieve 4Å | 56.5 |
| Molecular sieve 5Å | 50.2 |
| Alumnium Oxide ($Al_2O_3$) | 62.9 |

Preparation of Other 4H-chromene Derivatives

The new method of using molecular sieve 3Å, as disclosed herein, also was applied to the preparation of several 4H-chromene derivatives. The yields are shown in Table 2.

TABLE 2

Preparation Of 4-H-chromene derivatives using molecular sieve 3Å

| | $R_1$ | $R_2$ | $R_3$ | Yield* % |
|---|---|---|---|---|
| 3Å (HA14-1) | 6-Br | H | —$CH_2CH_3$ | 86.1 |
| 3b | 6-Br | H | —$C(CH_3)_3$ | 82.5 |
| 3c | 6-Br | H | —$CH_2Ph$ | 60.0 |
| 3d | 6-Br | H | —$CH_2CH_2OCH_3$ | 74.6 |
| 3e | 6-Cl | H | —$CH_2CH_3$ | 70.7 |
| 3f | 6-Cl | H | —$C(CH_3)_3$ | 74.8 |
| 3g | 6-Cl | H | —$CH_2CH_2OCH_3$ | 72.9 |
| 3h | 6-$NO_2$ | H | —$C(CH_3)_3$ | 84.0 |
| 3i | H | 8-$CH_2CH=CH_2$ | —$CH_2CH_3$ | 78.1 |
| 3j | H | 8-$CH_2CH=CH_2$ | —$CH_2CH_2CH_2CH_3$ | 85.3 |
| 3k | 5-Br | 8-$OCH_3$ | —$CH_2CH_3$ | 45.7 |
| 3l | 6-$NO_2$ | 8-$CH_2Br$ | —$CH_2CH_2CH_2CH_3$ | 51.3 |

*Isolated yield, without optimization

The present invention relates to a procedure for the synthesis of 4H-chromene derivatives. This method features mild reaction conditions, high yields, and facile manipulation. This novel methodology presented herein has been used to synthesize a series of HA14-1 analogs for investigating the structure-activity relationship of the analogs. The present invention thus provides a novel method for the optimization of synthesizing lead compounds for use in the development of novel therapeutic agents that will induce apoptosis.

While this invention has been described with a reference to specific embodiments, it will obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method for preparing a 4H-chromene derivative comprising the steps a) combining a salicylaldehyde derivative, an alkyl cyanoacetate and a suitable molecular sieve to form said 4H-chromene derivative; and b) isolating said 4H-chromene derivative.

2. The method of claim 1, wherein said salicylaldehyde derivative has a formula of:

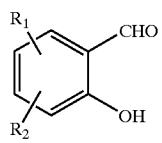

and said alkyl cyanoacetate has a formula of:

NC—$CH_2$—$COOR_3$ wherein, $R_1$ and $R_2$ are selected form the group consisting of hydrogen, $CH_2CH=CH_2$, $CH_2Br$, $OCH_3$, $NO_2$, Cl, and Br; and $R_3$ is selected from the group consisting of hydrogen, $CH_2CH_3$, $CH_2CH_2CH_2CH_3$, $C(CH_3)_3$, $CH_2Ph$ and $CH_2CH_2OCH_3$.

3. The method of claim 2, wherein said suitable molecular sieve is molecular sieve 3 Å.

4. The method of claim 1, wherein said 4H-chromene derivative is HA14-1, said salicylaldehyde derivative is 5-bromosalicylaldehyde, and said alkyl cyanoacetate is ethyl cyanoacetate.

5. A method of preparing a 4H-chromene derivative of a formula:

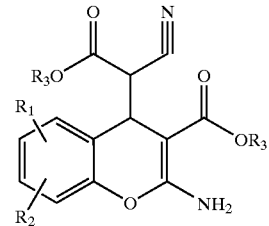

from a salicylaldehyde derivative of a formula:

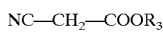

and an alkyl cyanoacetate of a formula:

NC—$CH_2$—$COOR_3$ wherein, $R_1$ and $R_2$ are selected from the group consisting of hydrogen, $CH_2CH=CH_2$, $CF_2Br$, $OCH_3$, $NO_2$, Cl, and Br; and $R_3$ is selected from the group consisting of hydrogen, $CH_2CH_3$, $CH_2CH_2CH_2CH_3$, $C(CH_3)_3$, $CH_2Ph$ and $CH_2CH_2OCH_3$;

comprising the steps of a) suspending said salicylaldehyde derivative in a first solvent;

b) combining said salicylaldehyde derivative suspension with said alkyl cyanoacetate to form a first reaction mixture;

c) adding a molecular sieve into said first reaction mixture to form a second reaction mixture;

d) stirring said second reaction mixture;
e) filtering off said molecular sieve from said second reaction mixture;
f) washing said filtered molecular sieve from step e) at least one time with a second solvent and collecting filtrates;
g) removing said second solvent from said filtrates from step f) to form a residue;
h) solidifying said residue; and
i) crystallizing said solidified residue.

6. The method of claim 5, wherein said molecular sieve comprises molecular sieve 3 Å.

7. The method of claim 6, wherein said first solvent is dry ethyl alcohol.

8. The method of claim 7, wherein said second solvent is tetrahydrofuran.

9. The method of claim 8, wherein the molar ratio of salicylaldehyde derivative:alkyl cyanoacetate is about 1:2.

10. The method of claim 5, wherein said 4H-chromene derivative is HA14-1, said salicylaldehyde derivative is 5-bromosalicylaldehyde, and said alkyl cyanoacetate is ethyl cyanoacetate.

* * * * *